(12) United States Patent
Samjitsingh

(10) Patent No.: US 12,297,911 B2
(45) Date of Patent: *May 13, 2025

(54) PRESSURE VALVE ASSEMBLY

(71) Applicant: Apalta Patents OÜ, Mõisa tn 4 (EE)

(72) Inventor: Sharon Samjitsingh, Rochester, NY (US)

(73) Assignee: APALTA PATENTS OÜ, Mõisa Tn 4 (EE)

(*) Notice: Subject to any disclaimer, the term of this patent is extended or adjusted under 35 U.S.C. 154(b) by 0 days.

This patent is subject to a terminal disclaimer.

(21) Appl. No.: 18/191,938

(22) Filed: Mar. 29, 2023

(65) Prior Publication Data

US 2023/0304586 A1 Sep. 28, 2023

Related U.S. Application Data

(63) Continuation of application No. PCT/US2021/053227, filed on Oct. 1, 2021.

(Continued)

(51) Int. Cl.
*F16K 1/38* (2006.01)
*A23P 30/20* (2016.01)
(Continued)

(52) U.S. Cl.
CPC ............. *F16K 1/38* (2013.01); *A23P 30/20* (2016.08); *B01J 4/002* (2013.01); *B01J 19/20* (2013.01);
(Continued)

(58) Field of Classification Search
None
See application file for complete search history.

(56) References Cited

U.S. PATENT DOCUMENTS 2,391,899 A * 1/1946 Hobbs ...................... F16K 1/42
251/333
3,819,292 A 6/1974 Wentworth
(Continued)

FOREIGN PATENT DOCUMENTS

WO WO-8301910 A1 6/1983
WO WO-9218236 A1 10/1992
(Continued)

OTHER PUBLICATIONS

International Search Report and Written Opinion issued in PCT/US2021/053227, mailed Feb. 15, 2022.
(Continued)

*Primary Examiner* — Umashankar Venkatesan
(74) *Attorney, Agent, or Firm* — WILSON SONSINI GOODRICH & ROSATI

(57) ABSTRACT

A valve assembly having a conical valve needle axially displaceable in a bore of a valve body wherein a portion of the larger diameter of the valve needle seats downstream at an annular ring when the valve is closed. There is an open area between one end of the valve body to the annular ring even at closure and nozzles for the input of a liquid. The inner wall of the valve body comprises at least one opening for the entry of a liquid under pressure following output of a slurry or liquid from a tube or pipe. The valve assembly is particularly useful in maintaining a semi-continuous or continuous pressurized flow of biomass from an extruder.

19 Claims, 7 Drawing Sheets

Related U.S. Application Data

(60) Provisional application No. 63/153,740, filed on Feb. 25, 2021, provisional application No. 63/146,608, filed on Feb. 6, 2021, provisional application No. 63/087,077, filed on Oct. 2, 2020.

(51) Int. Cl.
  *B01J 4/00* (2006.01)
  *B01J 19/20* (2006.01)
  *F16K 1/42* (2006.01)
  *F16K 17/06* (2006.01)
  *F16K 27/02* (2006.01)

(52) U.S. Cl.
  CPC .............. *F16K 1/42* (2013.01); *F16K 17/06* (2013.01); *F16K 27/0254* (2013.01); *B01J 2204/002* (2013.01)

(56) References Cited

U.S. PATENT DOCUMENTS

| | | | |
|---|---|---|---|
| 4,211,163 A * | 7/1980 | Brown | D21C 7/08 99/323.4 |
| 4,707,278 A | 11/1987 | Breyer et al. | |
| 5,277,879 A | 1/1994 | Elvin et al. | |
| 6,279,843 B1 | 8/2001 | Coldren et al. | |
| 7,000,856 B2 | 2/2006 | Mattes et al. | |
| 7,521,076 B1 | 4/2009 | Wenger et al. | |
| 7,819,976 B2 | 10/2010 | Friend et al. | |
| 7,976,259 B2 | 7/2011 | Craig et al. | |
| 8,858,065 B1 | 10/2014 | Vandalsem et al. | |
| 9,005,537 B1 * | 4/2015 | Cudahy | C10G 1/06 422/187 |
| 9,115,214 B2 * | 8/2015 | Nguyen | B30B 9/12 |
| 9,908,090 B2 | 3/2018 | Vandalsem et al. | |
| 9,981,416 B1 | 5/2018 | Vandalsem et al. | |
| 10,208,563 B2 * | 2/2019 | Volent | F16K 1/42 |
| 10,234,038 B2 | 3/2019 | Nagayo et al. | |
| 10,344,757 B1 | 7/2019 | Stark et al. | |
| 10,401,065 B2 | 9/2019 | Shimazu | |
| 10,442,995 B2 | 10/2019 | Felix et al. | |
| 10,844,413 B2 * | 11/2020 | Lumpkin | C12M 21/12 |
| 11,454,234 B2 * | 9/2022 | Vadasz Fekete | F16K 1/42 |
| 2006/0113406 A1 | 6/2006 | Ganser | |
| 2006/0280663 A1 | 12/2006 | Osato et al. | |
| 2007/0164143 A1 * | 7/2007 | Sabourin | D21D 1/306 241/297 |
| 2007/0237022 A1 | 10/2007 | Wiltz et al. | |
| 2009/0022570 A1 * | 1/2009 | Craig | C12M 33/16 414/197 |
| 2009/0221814 A1 | 9/2009 | Pschorn et al. | |
| 2010/0103769 A1 | 4/2010 | Bachman et al. | |
| 2010/0144001 A1 | 6/2010 | Horton | |
| 2010/0168927 A1 | 7/2010 | Burrows | |
| 2011/0240128 A1 | 10/2011 | Barbato et al. | |
| 2012/0094348 A1 * | 4/2012 | Pye | C13K 1/02 435/162 |
| 2012/0111714 A1 | 5/2012 | Court et al. | |
| 2012/0184721 A1 | 7/2012 | Wingerson et al. | |
| 2013/0210101 A1 | 8/2013 | Parekh et al. | |
| 2013/0323830 A1 | 12/2013 | Horton | |
| 2014/0106418 A1 | 4/2014 | Parekh et al. | |
| 2014/0110324 A1 | 4/2014 | Lehoux et al. | |
| 2014/0175335 A1 * | 6/2014 | Anderson | C10J 3/30 422/186.21 |
| 2014/0178944 A1 | 6/2014 | Parekh et al. | |
| 2014/0188543 A1 | 7/2014 | Pearlmutter et al. | |
| 2014/0262727 A1 | 9/2014 | Felix et al. | |
| 2014/0342423 A1 | 11/2014 | Parekh et al. | |
| 2015/0329927 A1 | 11/2015 | Parekh | |
| 2016/0032414 A1 | 2/2016 | Parekh et al. | |
| 2017/0226535 A1 | 8/2017 | Tudman | |
| 2018/0002451 A1 | 1/2018 | Ge et al. | |
| 2018/0079871 A1 | 3/2018 | Tudman | |
| 2019/0004078 A1 | 1/2019 | Ishii | |
| 2019/0040478 A1 | 2/2019 | Tudman et al. | |
| 2020/0030096 A1 | 1/2020 | Zeitani | |
| 2021/0131032 A1 * | 5/2021 | Hägglund | C08H 8/00 |
| 2021/0285155 A1 | 9/2021 | Tudman et al. | |
| 2023/0302424 A1 | 9/2023 | Samjitsingh et al. | |

FOREIGN PATENT DOCUMENTS

| | | |
|---|---|---|
| WO | WO-2010056940 A2 | 5/2010 |
| WO | WO-2010135902 A1 | 12/2010 |
| WO | WO-2015063876 A1 | 5/2015 |
| WO | WO-2015077885 A1 | 6/2015 |
| WO | WO-2017031141 A1 | 2/2017 |
| WO | WO-2019169364 A1 | 9/2019 |
| WO | WO-2019204696 A1 | 10/2019 |
| WO | WO-2020069519 A1 | 4/2020 |
| WO | WO-2022072870 A1 | 4/2022 |
| WO | WO-2022072872 A1 | 4/2022 |
| WO | WO-2022072873 A1 | 4/2022 |

OTHER PUBLICATIONS

International Preliminary Report on Patentability issued in PCT/US2021/053227, dated Mar. 28, 2023.
International Preliminary Report on Patentability issued in PCT/US2021/053229, dated Mar. 28, 2023.
International Preliminary Report on Patentability issued in PCT/US2021/053230, dated Mar. 28, 2023.
International Search Report and Written Opinion issued in PCT/US2021/053229, mailed Feb. 11, 2022.
International Search Report and Written Opinion issued in PCT/US2021/053230, mailed Dec. 10, 2021.
U.S. Appl. No. 18/192,054 Office Action dated Jun. 17, 2024.

* cited by examiner

PRESSURE VALVE ASSEMBLY

CROSS-REFERENCE

This application is a continuation of International Application No. PCT/US2021/053227, filed on Oct. 1, 2021, which claims the benefits of U.S. Provisional Application No. 63/087,077, filed on Oct. 2, 2020, U.S. Provisional Application No. 63/146,608, filed on Feb. 6, 2021, and U.S. Provisional Application No. 63/153,740, filed on Feb. 25, 2021, each of which is incorporated herein by reference in its entirety.

BACKGROUND

Valves are used to control the flow of materials in many industrial processes. The inside of a relief valve contains a plug that blocks or reduces the output of a source of material when the valve is pressurized. When the pressure behind the plug is released the plug is pushed back by the force of the pressure from this output. This allows the valve to be opened until the pressure behind the plug is equal or greater than the force of the output. If a valve is coupled to an actuator operating in response to the output, precise continuous movement is possible rather than with just a manual-operated or spring-operated valve.

When moving materials under pressure it can be difficult to control the pressure in the container through which they are transported. This is difficult for continuous or semi-continuous flow of a slurry of materials moving in one direction in critical operating states resulting from treatment of the media. In order to maintain a constant pressure and velocity of the moving material, a valve must be designed to operate to hold the pressure in the pipe or barrel at a constant while allowing for a certain velocity. This is especially true of particulate substances such as biomass moving in a liquid under high pressure where the valve is involved in further treatment and the flow of materials is rapid and surging. Such severe operating conditions can induce premature failure and leakage of the valve assembly, resulting in blowouts and extreme wear. Further, slurry particles can become trapped in the valve sealing cycle, resulting in performance degradation of the valve assembly. In general, pressure relief valves are not designed to handle such operations.

SUMMARY

In one aspect, provided herein is a valve assembly comprising a valve body having an input end, a discharge end, and a chamber formed therein in connection with the input end and the discharge end, the input end attachable to a tube with a fluid or slurry input that flows through the valve assembly; a conical valve needle that has a cone with a wide end opposing to its conical tip and is axially displaceable in the chamber within the valve body; and a housing attached to the discharge end of the valve body and enclosing the valve needle when the valve needle is disengaged with the valve body; wherein the valve needle has a diameter at the wide end that is at least 4% larger than an inner diameter of the valve body at its discharge end.

In some embodiments, the valve body has an annular ring that sits in a recessed cavity on an internal surface of the valve body at the discharge end. In some embodiments, the annular ring is replaceable. In some embodiments, an internal surface of the annular ring aligns with the internal surface of the valve body. In some embodiments, the valve needle sits at the annular ring when closed in the valve body. In some embodiments, the housing comprises therein a detachable discharge ring that sits adjacent to the discharge end of the valve body. In some embodiments, the discharge ring has a tapered shape. In some embodiments, the valve body comprises nozzles for input of a liquid. In some embodiments, the chamber of the valve body forms a part of a reaction zone with the tube for a biomass pretreatment process. In some embodiments, the tube is an extruder. In some embodiments, the extruder is a twin screw extruder. In some embodiments, the valve needle is operably linked to an actuator via a shaft. In some embodiments, the actuator maintains a pressure on the valve needle. In some embodiments, the actuator maintains a pressure of over 1,800 lbf on the valve needle. In some embodiments, the actuator maintains a pressure of between 50,000 to 500,000 lbf on the valve needle. In some embodiments, the valve body has a circular section at the discharge end, a circular collar at the input end that is smaller in inner diameter than the circular section at the discharge end, and an intercalary conical section therebetween. In some embodiments, there is an annular space formed in the chamber between the valve needle and the valve body when the valve needle is closed on the valve body. In some embodiments, the housing comprises a discharge pipe. In some embodiments, an inner diameter of the housing at an end of the housing abutting the valve body is at least 7% larger than an inner diameter of the valve body at its discharge end. In some embodiments, an inner diameter of the housing at an end of the housing abutting the valve body is about 7% larger than an inner diameter of the valve body at its discharge end. In some embodiments, the cone of the conical valve needle is tapered in a range of from about 45 degrees to about 75 degrees. In some embodiments, the cone of the conical valve needle is tapered about 45 degrees.

In another aspect, provided herein is a valve assembly comprising: a valve body comprising a large circular section, an intercalary conical section, and a small circular collar containing one or more nozzles for liquid input, the valve body having a chamber formed therein that connects an input end and a discharge end of the valve body, wherein the small circular collar is smaller in inner diameter than the large circular section; a valve needle axially displaceable within the chamber of the valve body; and a housing attached to the discharge end of the valve body and enclosing the valve needle when the valve needle is disengaged with the valve body.

In another aspect, provided herein is a system for treating biomass through an extruder comprising: an extruder comprising one or more screws wherein an internal plug of biomass is formed due to action of the screws, thereby forming one end of a pressurized reaction zone; a means for supplying steam and chemicals to the reaction zone; and a valve assembly at an output end of the extruder that forms a downstream end of the reaction zone and adds a liquid to the reaction zone; wherein the valve assembly is capable of rapidly discharging pressurized treated biomass into a non-pressurized discharge area.

In one aspect, a valve assembly comprising a housing, a valve body, and a valve needle attached to a tube with an output that flows through the valve assembly is provided, wherein the valve comprises: a conical valve needle which is axially displaceable in an annular space of the valve body and on one end has a conical valve needle tip; and wherein the downstream inner diameter of the valve body is at least 4% larger than the inner wall of the housing. In one embodiment, the valve assembly has an annular ring that is part of the valve body and is replaceable.

In another embodiment, the valve assembly housing contains a detachable discharge ring. In another aspect, the valve body contains nozzles for the input of a liquid. In a further embodiment, the valve needle seats when closed in the valve body at the discharge ring. In one aspect, the valve assembly forms a part of a reaction zone with the tube. In a further aspect, the valve needle is attached to an actuator. In one embodiment, the actuator maintains a pressure on the valve needle, said pressure which is maintained over 1,800 lbf on the valve needle. In another embodiment, the actuator maintains a pressure of between 50,000 to 500,000 lbf on the valve needle.

In one aspect, the tube attached to the valve assembly is an extruder. In a further aspect, the extruder is a twin screw extruder.

In another embodiment, a conical valve needle for engagement with a valve body that comprises a valve needle that extends beyond the valve body into a discharge area when the valve is closed is provided. In one aspect, an annular ring is part of the valve body. In another aspect, the valve needle seats downstream of the annular ring. In a further aspect, the annular ring is replaceable. In one embodiment, a housing is attached downstream to the valve body containing a valve needle and the housing contains a detachable discharge ring. In another embodiment, the valve body contains nozzles for the input of a liquid. In another embodiment, the valve needle seats when closed in the valve body at the discharge ring. In a further aspect, the valve body and valve needle form a part of the reaction zone with the tube. In another aspect, the valve needle is attached to an actuator. In a further aspect, the actuator maintains a pressure on the valve needle. In a further aspect, the actuator maintains a pressure of over 1,800 lbf on the valve needle. In one embodiment, the actuator maintains a pressure between 50,000 to 500,000 lbf on the valve needle.

In one embodiment, the valve needle is in a valve body attached to an extruder. In a further embodiment, the extruder is a twin screw extruder.

In one embodiment is provided a valve assembly that becomes part of a reaction zone when attached to a tube or pipe. In another embodiment, the pipe or tube is an extruder. In a further embodiment, the extruder is a twin screw extruder. In another embodiment, at least part of the contents of the extruder are under pressure.

In one embodiment, a valve assembly is provided, wherein the pressurized zone of a tube or pipe or extruder extends into the valve assembly. In another embodiment, a valve assembly that has an increase in internal diameter between the end of the valve body where material is discharged and the diameter of the discharge housing.

In one aspect a valve assembly is provided for use in the pressurized passage of a fluid, slurry or other materials comprising a housing and a valve body comprising: a large circular section; a middle conical section; and a smaller circular collar section containing one or more nozzles for liquid input; and a valve needle. In another aspect the housing contains a removable discharge ring. In a further aspect, the discharge ring is tapered. In another aspect, the valve body contains an annular ring. In another aspect, the annular ring is removable. In another embodiment, there is a space between the valve body and the valve needle when the valve needle is seated. In a further embodiment, the nozzles for liquid input transfer water into the space between the valve body and the valve needle. In a further embodiment, the nozzles for liquid input transfer a liquid other than water into the space between the valve body and the valve needle. In a further embodiment, the liquid is selected from the group consisting of: an acid, a base, an alcohol, a ketone, an aldehyde, a solvent, or a combination thereof.

In another embodiment, a system for treating biomass through an extruder is provided comprising: an extruder comprising one or more screws wherein an internal plug of biomass is formed due to action of the screws, thereby forming one end of a pressurized reaction zone; a method of supplying steam and chemicals to the reaction zone; a valve assembly at the output end of the extruder that forms the downstream end of the reaction zone and adds a liquid to the reaction zone and is capable of rapidly discharging pressurized treated biomass into a non-pressurized discharge area. In another aspect, the biomass is selected from the group consisting of: silage, agricultural residues, corn stover, bagasse, sorghum, nuts, nut shells, coconut shells, Distillers Dried Solubles, Distillers Dried Grains, Condensed Distillers Solubles Distillers Wet Grains, Distillers Dried Grains with Solubles, woody materials, sawdust, wood chips, timber slash, mill scrap, municipal waste, waste paper, recycled toilet papers, yard clippings, and energy crops such as poplars, willows, switchgrass, alfalfa, and prairie bluestem, non-woody plant matter, cellulosic material, lignocellulosic material, hemicellulosic material, carbohydrates, corn, sugar cane, grasses, switchgrass, high biomass sorghum, bamboo, corncobs, and peels and pits. In a further aspect, the biomass is treated for less than 60, 55, 50, 45, 40, 35, 30, 25, 20, 19, 18, 17, 16, 15, 14, 13, 12, 10, 9, 8, 7, 6, 5, 4, 3, 2, or 1 seconds in the reaction zone. In one embodiment, the temperature in the reaction zone is elevated to 50-500° C., 75-400° C., 100-350° C., 150-300° C., 200-250° C., 150-300° C., 50-1000 PSI, 100-750 PSI, 200-600 PSI, 300-500 PSI or 350-450 PSI. In another embodiment, the chemical is an acid. In a further embodiment, the acid is sulfuric acid.

In one aspect there is provided a system, wherein a valve assembly comprises a housing, and a valve body comprising: a large circular section; a middle conical section; a smaller circular collar containing one or more nozzles for liquid input; and a valve needle. In another aspect, the system has a valve assembly wherein the housing contains a removable discharge ring. In a further aspect, the discharge ring of the valve assembly is tapered. In another embodiment, the valve body of the valve assembly contains an annular ring. In a further embodiment, the annular ring is removable. In another aspect, the valve body contains a space between the valve body and the valve needle when the valve needle is seated. In another embodiment, the valve assembly comprises nozzles for liquid input and transfer water into the space between the valve body and the valve needle. In a further embodiment, the nozzles for liquid input transfer a liquid other than water into the space between the valve body and the valve needle. In a further embodiment, the liquid comprises an acid, a base, an alcohol, a ketone, an aldehyde, a solvent, or a combination thereof.

In one embodiment, there is provided a method for treating a slurry or liquid in a pipe or barrel comprising: a pipe or barrel with a plug forming one end of a reaction zone, moving a liquid or slurry through the pipe or barrel, using a valve assembly attached to the output end of the pipe or barrel to form the downstream end of the reaction zone while maintaining pressure in the reaction zone, adding a liquid into the upstream end of the valve assembly as the liquid or slurry enters the valve assembly, and using the valve assembly to discharge treated liquid or slurry into a non-pressurized area.

In one embodiment, a valve assembly attached to a pipe or barrel is provided that inputs a liquid into the valve body after output of a liquid or slurry from the pipe or barrel but before said liquid or slurry reaches the valve needle.

In one embodiment, a valve assembly is provided wherein the valve body has a removable annular ring adjacent to a removable discharge ring in the discharge housing. In another embodiment, the discharge ring of the valve assembly is tapered.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
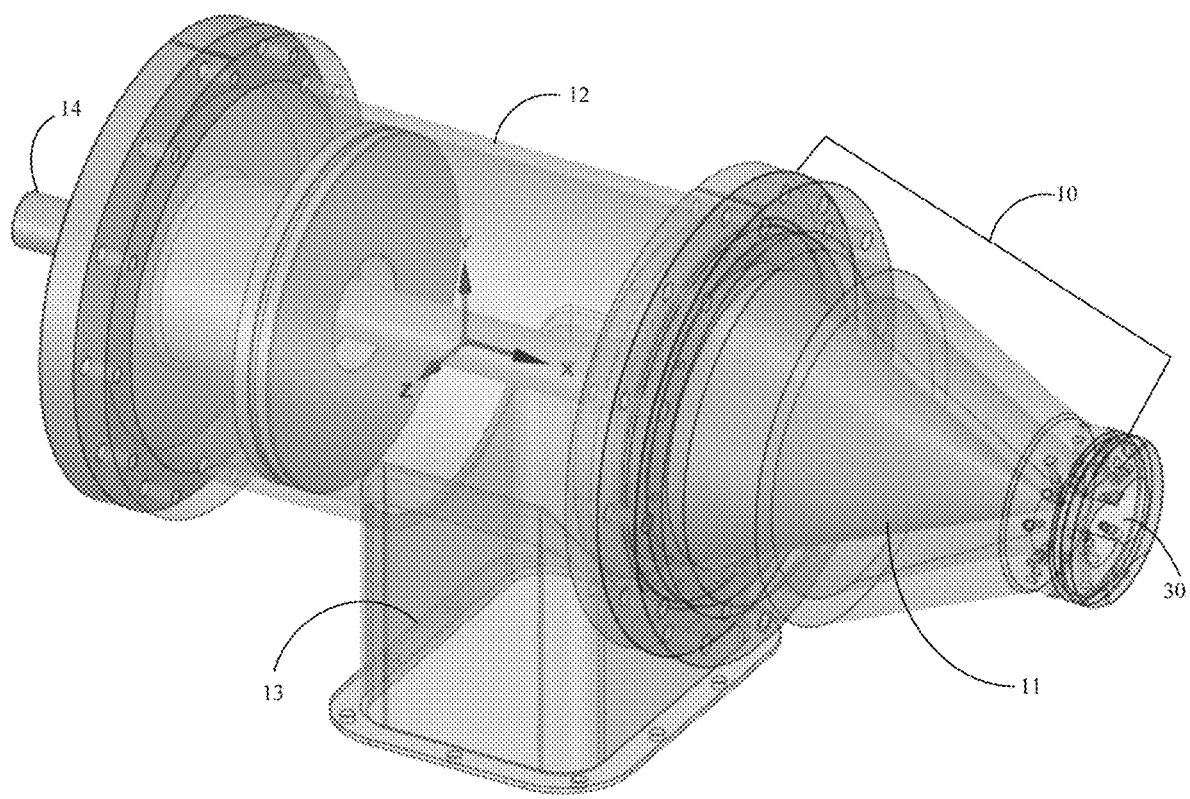
FIG. 1 is a diagram depicting the modified pressure valve assembly.

As used in the specification and the appended claims, the singular forms "a," "an" and "the" include plural referents unless the context clearly dictates otherwise. Thus, for example, reference to "a purified monomer" includes mixtures of two or more purified monomers. The term "comprising" as used herein is synonymous with "including," "containing," or "characterized by," and is inclusive or open-ended and does not exclude additional, unrecited elements or method steps.

"About" means a referenced numeric indication plus or minus IO % of that referenced numeric indication. For example, the term about 4 would include a range of 3.6 to 4.4. All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise. Therefore, "for example ethanol production" means "for example and without limitation ethanol production."

In this specification and in the claims that follow, reference will be made to a number of terms which shall be defined to have the following meanings.

Definitions

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

Unless characterized otherwise, technical and scientific terms used herein have the same meaning as commonly understood by one of ordinary skill in the art.

The term "biomass" as used herein has its ordinary meaning as known to those skilled in the art and can include one or more carbonaceous biological materials that can be converted into a biofuel, chemical or other product. Biomass as used herein is synonymous with the term "feedstock" and includes silage, agricultural residues (corn stalks, grass, straw, grain hulls, bagasse, etc.), nuts, nut shells, coconut shells, animal waste (manure from cattle, poultry, and hogs), Distillers Dried Solubles, Distillers Dried Grains, Condensed Distillers Solubles, Distillers Wet Grains, Distillers Dried Grains with Solubles, woody materials (wood or bark, sawdust, wood chips, timber slash, and mill scrap), municipal waste (waste paper, recycled toilet papers, yard clippings, etc.), and energy crops (poplars, willows, switchgrass, alfalfa, prairie bluestem, algae, including macroalgae such as members of the Chlorophyta, Phaeophyta, Rhodophyta, etc.). One exemplary source of biomass is plant matter. Plant matter can be, for example, woody plant matter, non-woody plant matter, cellulosic material, lignocellulosic material, hemicellulosic material, sugar cane, grasses, switchgrass, sorghum, high biomass sorghum, bamboo, algae and material derived from these. Plants can be in their natural state or genetically modified, e.g., to increase the cellulosic or hemicellulosic portion of the cell wall, or to produce additional exogenous or endogenous enzymes to increase the separation of cell wall components. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corncobs, corn fiber, corn steep solids, distillers' grains, peels, pits, fermentation waste, straw, lumber, sewage, garbage and food leftovers. Peels can be citrus which include, but are not limited to, tangerine peel, grapefruit peel, orange peel, tangerine peel, lime peel and lemon peel. These materials can come from farms, forestry, industrial sources, households, etc. Another non-limiting example of biomass is animal matter, including, for example milk, bones, meat, fat, animal processing waste, and animal waste. "Feedstock" is frequently used to refer to biomass being used for a process, such as those described herein.

"Pretreatment" or "pretreated" is used herein to refer to any mechanical, chemical, thermal, biochemical process or combination of these processes whether in a combined step or performed sequentially, that achieves disruption or expansion of the biomass so as to render the biomass more susceptible to attack by enzymes and/or microbes, and can include the enzymatic hydrolysis of released carbohydrate polymers or oligomers to monomers. In one embodiment, pretreatment includes removal or disruption of lignin so as to make the cellulose and hemicellulose polymers in the plant biomass more available to cellulolytic enzymes and/or microbes, for example, by treatment with acid or base. In one embodiment, pretreatment includes disruption or expansion of cellulosic and/or hemicellulosic material. In another embodiment, it can refer to starch release and/or enzymatic hydrolysis to glucose. Steam explosion, and ammonia fiber expansion (or explosion) (AFEX) are well known thermal/chemical techniques. Hydrolysis, including methods that utilize acids, bases, and/or enzymes can be used. Other thermal, chemical, biochemical, enzymatic techniques can also be used.

"Steam explosion" as used herein is a physicochemical method that uses high-pressure steam to disrupt bonding between polymeric components and decompression to break the lignocellulose structure. In this method, the lignocellulose slurry is treated with high-pressure steam for some time and then rapidly depressurized to atmospheric pressure.

As intended herein, a "liquid" composition may contain solids and a "solids" composition may contain liquids. A liquid composition refers to a composition in which the material is primarily liquid, and a solids composition is one in which the material is primarily solid. A "slurry" refers to solids dissolved or undissolved in a liquid.

DESCRIPTION

The following description and examples illustrate some exemplary embodiments of the disclosure in detail. Those of skill in the art will recognize that there are numerous variations and modifications of this disclosure that are encompassed by its scope. Accordingly, the description of a certain exemplary embodiment should not be deemed to limit the scope of the present disclosure.

In one aspect, the valve assembly described herein have a structure and design that addresses degradative stresses encountered in high pressure flows of treated liquids or slurries of materials flowing through a tube or pipe. The valve assembly is designed to incorporate part of the treatment of such liquids or slurries as the flow passes from the attached tube or pipe upstream into the valve assembly, through the valve assembly and downstream into a discharge area.

In one embodiment, valve assemblies for use in fluid ends are provided. In another aspect, the valve assembly disclosed herein can be used to continuously or semicontinuously process liquids, a slurry of materials, a thick liquid, or any liquified matter under pressure. By process, it is understood that materials can be modified alone by means of heat, pressure, and/or the addition of chemicals, or mixed under pressure, heated, chemically reacted by means of combining two or more components (simultaneously or through subsequent addition), by the addition of chemical components such as acids, bases, bleaching components, dyes, and the like. Examples of such components include plastics, plant materials, foodstuffs, polymers, polyurethanes, and the like.

In one aspect, a slurry of materials can include pretreated biomass or partially-hydrolyzed biomass. This arrangement can be used to obtain a constant velocity and pressure as material is moved through a passageway such as a tube or pipe. Water or steam can be added to increase and maintain a constant pressure in the passageway by means of an intercalary plug and the valve assembly at the output. The section between the plug and through the valve assembly is the reaction zone wherein modifications to the materials occur. This zone includes the flashing of materials through the end of the valve needle.

In one embodiment, an extruder and valve assembly can be used to process materials. Extruders move liquids, slurries, solid and viscous materials through a barrel by means of screw elements. Depending on the shape of the elements, materials may be slowed, mixed, or pushed through the barrel. The extruder can be a single screw extruder, a twin-screw extruder, or a triple-screw extruder. Preferably, for biomass materials, a twin-screw extruder is used. Extruders having specially configures screws designed to permit the addition of very high quantities of steam for increased pressure make it possible to pretreat biomass at high velocities. A rapid extruder pretreatment system, such as described in US 2016/0273009 A1 or WO2018/151833 (A1), each incorporated herein by reference in its entirety, offers a unique pathway for the deconstruction of biomass and release of cellulose and lignin from other biomass components. The combination of mechanical fibrillation, dilute acid hydrolysis, and steam explosion, all accomplished in under 20 seconds, yields a very clean slurry of soluble sugars, microcrystalline cellulose, and lignin. The short, yet intense, treatment duration yields a unique cellulose, hemicellulose and lignin products that have been rendered into a highly reactive states without the overcooking or sulfonation that occurs in most other processes.

Restriction and relief devices for liquids and materials moving through pipes or barrels have been proposed in the past. Several of these have involved intercalary valves in an extruder barrel itself. One such device described in US 2007/0237022A1 is a mid-barrel adjustable valve assembly. Others are end valves such as those found in US2009/0053800A1, WO2010/056940A2, or U.S. Pat. No. 10,344,757B1. None of these function as a part of the treatment system and are not capable of high velocity continuous processing.

Extrusion may be continuous or semi-continuous and the process can be done with the material hot or cold. Commonly extruded materials include metals, polymers, ceramics, concrete, modelling clay, and foodstuffs, however, biomass can be processed in an extruder as well. Extruders can have one or more shafts. A twin-screw extruder is a machine having two co-penetrating and self-cleaning identical screws which are mounted on shafts and rotate in the same direction in a fixed closed housing called "barrel". The twin-screw extruders can operate continuously with very short residence times under high temperatures and pressures.

In one embodiment, an acid, heat and explosion pretreatment process to extract biomass components is a rapid treatment process that includes steam explosion. The treatment is carried out as reduced-size particles of biomass are treated to pressurized acid hydrolysis and high temperatures through steam, then subjected to steam explosion. Because the whole process is uniform throughout and only takes seconds, it requires an effective and rapidly moving valve system to maintain pressures for continuous processing.

In processing biomass, steam is injected into the barrel to increase temperature and pressure. In one embodiment, the screw elements also function to slow down the flow of materials to form an intercalary plug that functions to seal materials in the barrel after input and further build pressure within the barrel. See, e.g., U.S. application Ser. No. 15/932,340, incorporated herein by reference.

The example of the valve assembly is not meant to be limiting to an extruder but is provided as an illustration of demonstrating its functional value. In this system, one functional embodiment of the pressure valve assembly is to help initiate and maintain constant pressure in the extruder and through the valve body. This is the reaction zone through which much of the treatment of the biomass takes place. The intercalary plug in the extruder facilitates slowdown through the use of particular screws and steam is used to build the pressure in the reaction zone. An actuator sets the pressure on the valve needle to keep the required pressure in the extruder and within the valve body. If a valve is coupled to an actuator operating in response to the internal pressure at the end of the pipe or barrel instead of a manual or spring-operated valve, precise continuous movement is possible.

Preferably, the actuator is a hydraulic or pneumatic actuator such as those manufactured by Kyntronics (Solon, OH 44139, U.S.A.). The actuator keeps the valve needle moving in and out endlessly and quickly with very small movements along the longitudinal axis. The actual force the needle valve must maintain for biomass in the reaction zone of the body of the extruder barrel can range from 1,800 lbf to 82,000 lbf and much higher (over 500,000 lbf). Constant force is achieved by controlling the annular space through which treated biomass material or liquid flows. An actuator system takes an electrical signal directly to the actuation mechanism. It is set to work at a particular pressure and react to the force exerted by the material flowing out of the tube or extruder.

In one aspect, because the reaction zone encompasses the area between the plug, through the valve body, and the steam explosion area as liquid or slurry flashes outside the annular ring (the interface between the annular and discharge ring —see infra), a shorter reaction zone length is required in the tube or pipe. In the example of biomass processing in an extruder, this shortens the length of the extruder reaction zone and reduces the cost of the metallurgy necessary for extruder processing.

Figure 2:
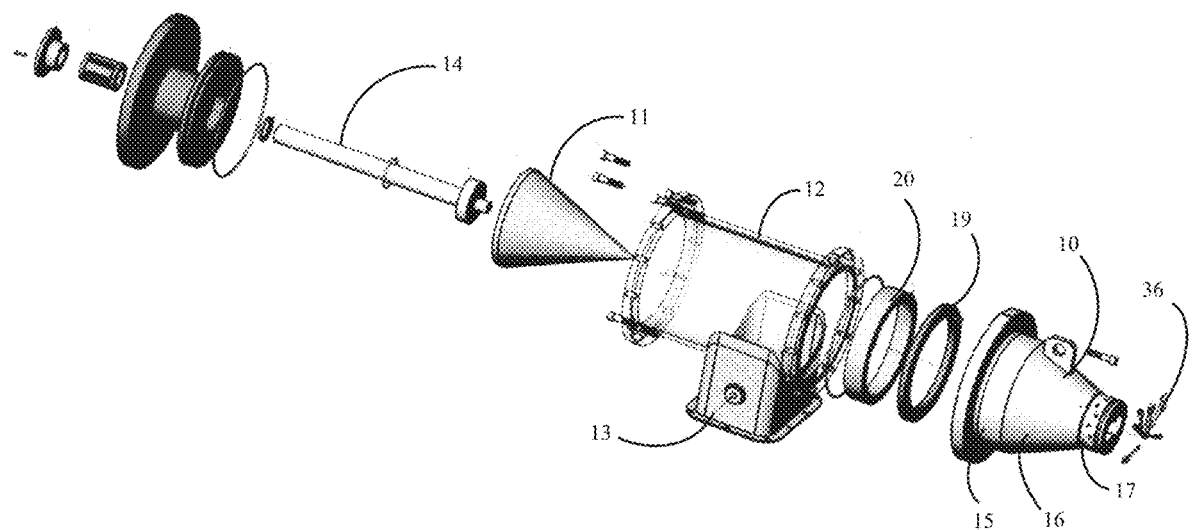
FIG. 2 is a diagram showing a longitudinal view of the valve and its housing.

In one example of a pressure valve assembly, as shown in FIG. 1, the valve has a valve body 10 fitted with a conical valve needle 11 and a housing 12 fitted with a discharge pipe 13. The valve body and needle can be made of any material that can withstand the wear and tear of liquids or slurries of different chemicals passing through from upstream input 30 through the valve body and housing to the discharge pipe 13, but it is constructed of an inert metal or metal with an inert coating. The valve needle is attached to a shaft 14. The valve body 10 as shown in a longitudinal section in FIG. 2, has a cylindrical-shaped section 15, an intercalary conical section 16, and another generally cylindrical-shaped collar 17 of smaller diameter than the first section 15. The valve body includes an annular (wear) ring 19 at its widest part. It sits into a recessed cavity in the valve body section 15. The annular ring 19 internal surface aligns with the rest of the valve body 10 and functions as a wear part that can be replaced. The annular ring 19 sits inside the reaction zone of the valve and extends to the minimum annular space 21 (see FIG. 7A) after which the flash to atmosphere (steam explosion) occurs.

The tapered discharge ring 20 sits outside the valve body 10 in the housing 12 and is not a part of the reaction zone. It is a means to ensure liquids or slurry are channeled to the discharge pipe 13 and into the flash tank (not shown). It is also made a wear part so that it is easily changed. The taper on the discharge ring 20 (see FIGS. 3A and 3B) avoids a right angle connection to the valve body that could result in material build up and interfere with movement of substances flowing from the needle tip to the output.

Figure 3A:
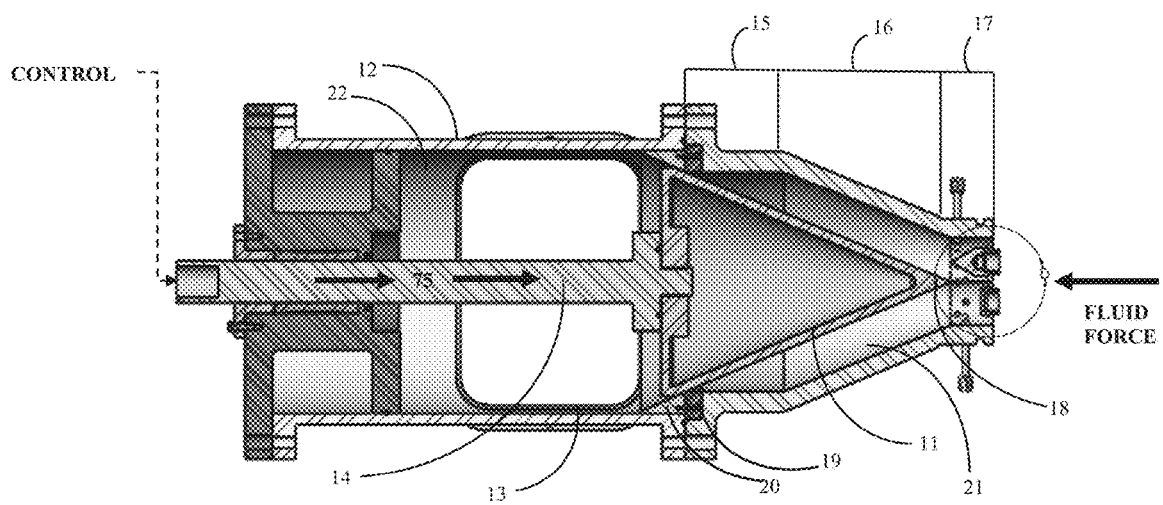
FIGS. 3A and 3B are diagrams depicting longitudinal views of the valve assembly from the top (FIG. 3A) and side (FIG. 3B).
Figure 3B:
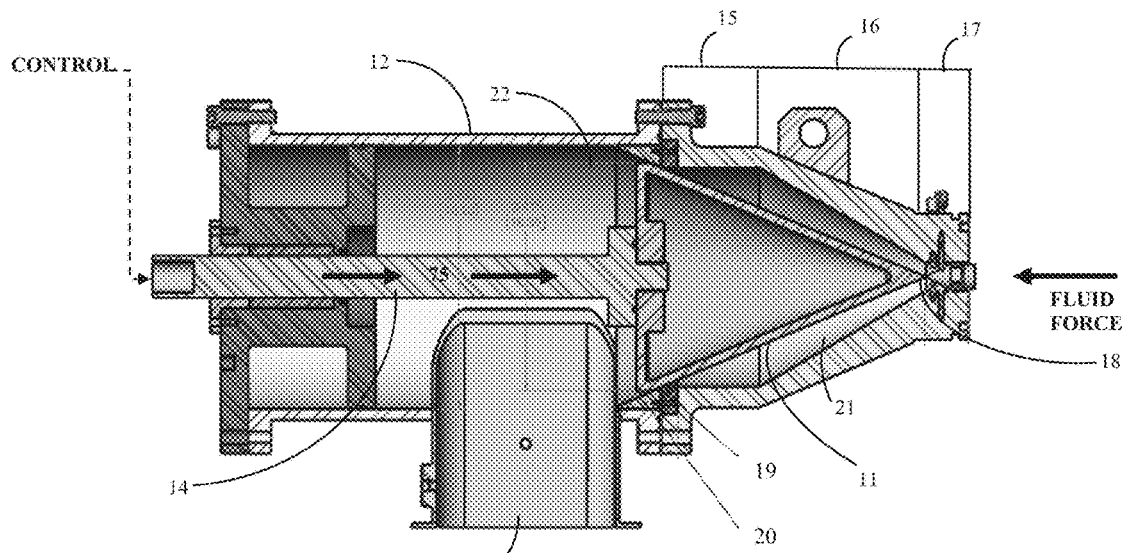

FIGS. 3A and 3B are longitudinal sections of the top and side view, respectively, of the valve and its housing. Materials flow upstream under pressure from a tube, barrel or pipe (FLUID FORCE) into section 17 through the valve body and are discharged downstream into the housing 12. Force from the actuator is applied to the valve needle through the shaft 14.

There is an annular space 21 between the valve body 10 and the valve needle 11. There is also a 7% increase in the diameter of the cavity 22 of the housing 12 where discharged liquid or slurries (materials) are received as compared to the internal diameter of the valve body 10 where materials flash out.

In operation, differential pressure acting on the valve needle 11 causes the valve needle 11 to be displaced along its longitudinal axis 75. The pressure behind the valve shaft 14 causes the valve to seat into the valve body section 15 just before the widest end of the needle 11.

The widest part of the needle valve 11 is slightly larger than the widest part of the valve body 10 so that it seats in the valve body section 15 at the annular ring 19 when closed. In one embodiment, the diameter of the wide end of the needle is at least 4% larger than the diameter of the valve body at the discharge end. In one embodiment, the diameter of the wide end of the needle is about 4% larger than the diameter of the valve body at the discharge end. In one embodiment, the diameter of the wide end of the needle is 416 mm while the diameter at the discharge end of the valve body is 400 mm. It can be made larger or smaller. In one embodiment, the cone is tapered 45 degrees from its widest diameter to the needle tip 18. In other embodiments, the taper of the cone can range from 45 degrees to 75 degrees. This measurement will be based on materials, feedstock, process requirements, space requirements, and the force necessary to move the needle valve.

Figure 4:
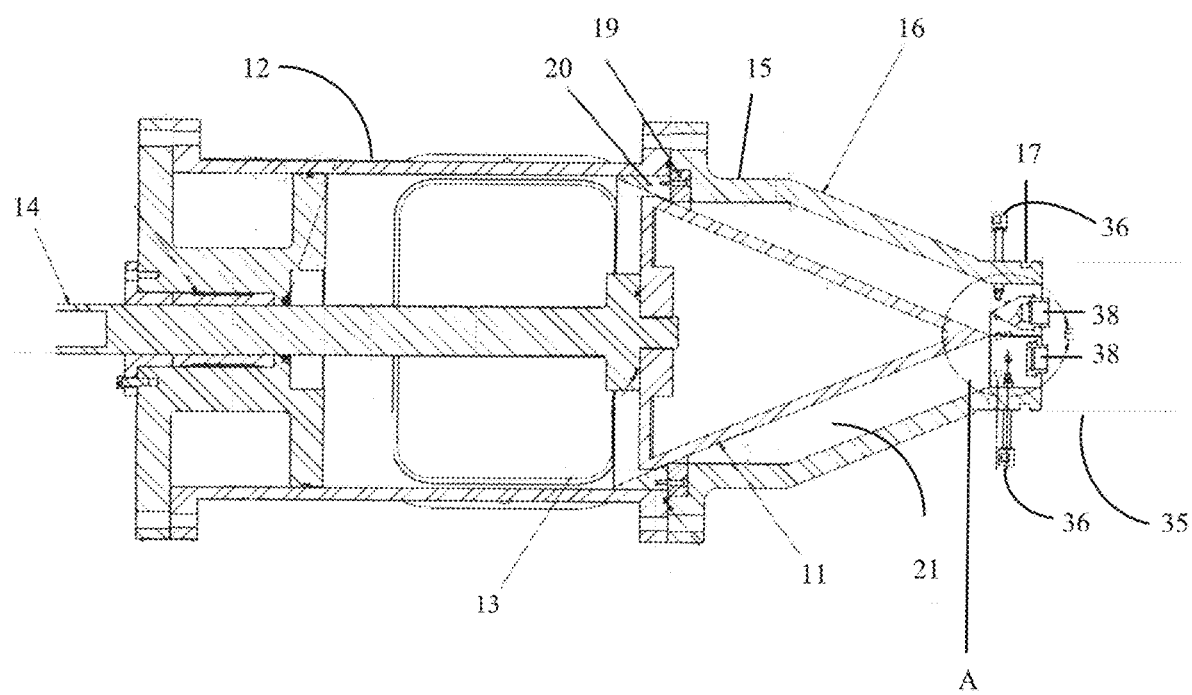
FIG. 4 is a longitudinal drawing of the valve assembly from in a view from the top.
Figure 5:
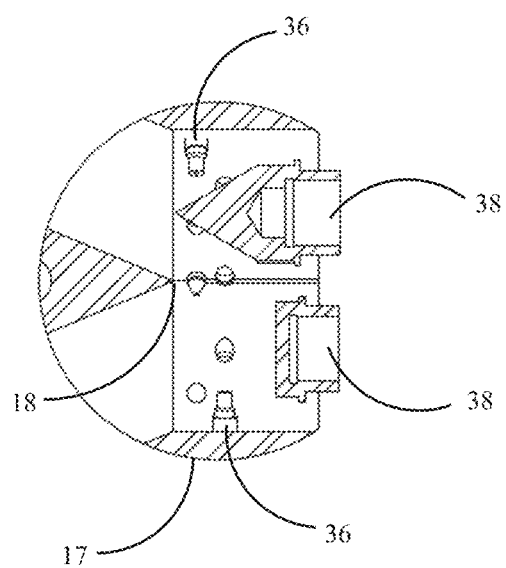
FIG. 5 is a larger drawing of section A seen in FIG. 4.

The collar 17 is the means by which the pressure relief valve is connected to an extruder or other tube. When the valve is fully seated and an extruder is attached, the valve needle tip 18 extends just to the beginning of the collar at the end of the conical section 16 and there is a space between the tip of the needle and the discharge end of the pipe or extruder 35 and the end of any screws 38. In the process of pretreating biomass in an extruder, water is injected through injection nozzles 36 in the collar 17 after the materials leave the extruder but before they reach the valve needle tip 18 (see FIGS. 4 and 5). The water is used to thin the material, improve rheology through steam explosion and therefore reduces torque on the extruder to push through the valve. With processing, materials, especially slurries, do not often flow, but surge a bit as they are processed through a pipe or barrel. The flow at exit is turbulent and as it mixes with the water, it smooths into a laminar flow traveling downstream in the space of the valve 21. Any liquid can be added just prior to output from the tube to facilitate the flow of materials through the valve system and/or to further process materials. In one embodiment, liquids such as water, acid, bases, alcohols, solvents, aldehydes, ketones, and the like can be used for this purpose.

In the closing position of the valve, the valve needle tip 18 comes to rest in the inner space of the valve body 10 and about at the interface of the intercalary conical section 16 and smaller cylindrical-shaped collar 17. See FIG. 5. The valve needle tip 18 is about 3-6 mm downstream of liquid injection.

Figure 6:
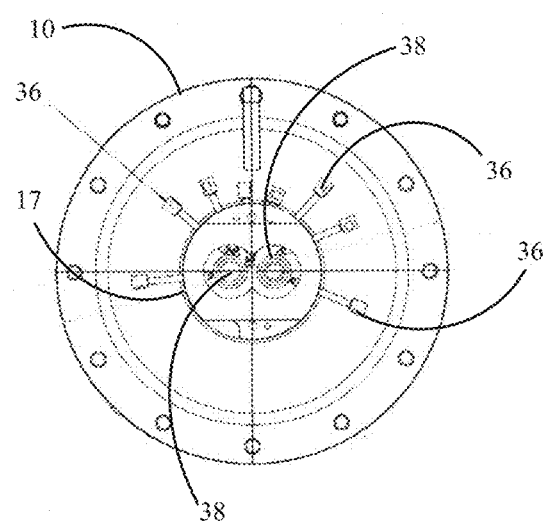
FIG. 6 is a drawing of a cross section of the valve body without the valve needle.

FIG. 6 is a cross section diagram of the valve body 10 without the valve needle 18 looking towards the discharge end of an extruder with twin screws 38. The input nozzles 36 eject liquid into the collar 17 after materials exit the extruder.

Figure 7A:
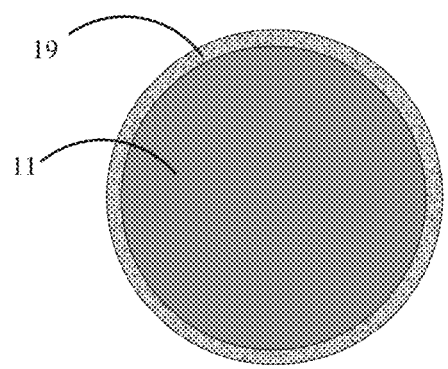
FIGS. 7A-7D depict cross sections of the valve at the annulus at: a closed position (FIG. 7A); with a 0.5 mm stroke (FIG. 7B); with a 1.0 mm stroke (FIG. 7C); and with a 1.5 mm stroke (FIG. 7D).
Figure 7B:
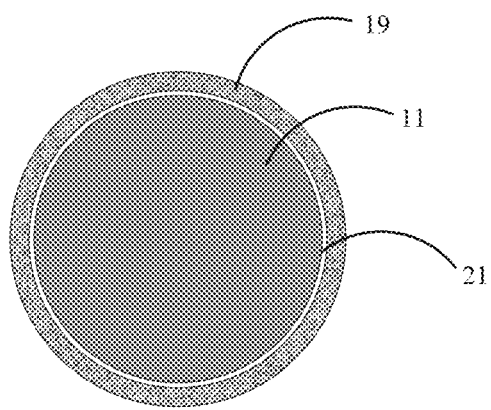
Figure 7C:
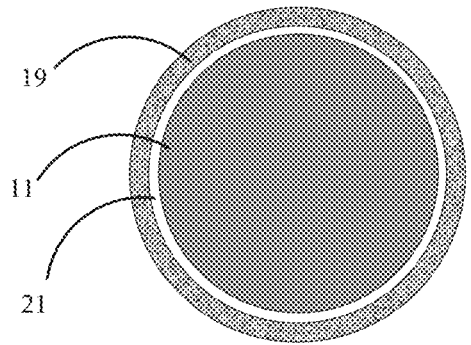
Figure 7D:
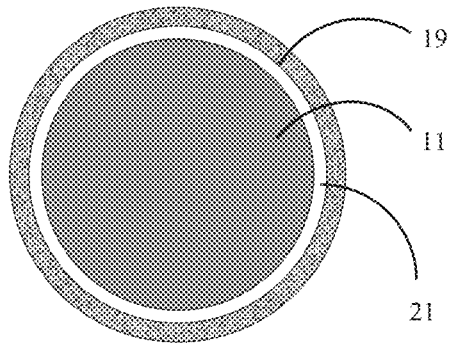

FIG. 7A is a cross section diagram of the seal between the conical needle 11 and the conical valve body 15 at the annular ring 19. At this point, the pressure behind the valve shaft 14 is equal to or greater than the pressure of the fluids and/or materials flowing out of the pipe and serves to stop the flow. FIG. 7B depicts the movement of the valve needle 11 when the pressure inside the pipe increases and the valve needle 11 moves approximately 0.5 mm towards the housing. The valve needle 11 is separated from its seated position in the annular ring 19 so that the fluids and/or materials can flow around the valve needle 11 through the passageway 21 towards the discharge area 22 (shown in FIG. 3). An increase in pressure from the pipe results in further movement of the valve needle 11 towards the discharge area, widens the gap between the needle and the annular ring 19, and allows a greater flow of fluids and/or materials; i.e., movement at 1.0 mm (FIG. 7C), and 1.5 mm (FIG. 7D).

In operation, the valve needle 18 moves in and out several times per second to maintain the setpoint pressure required, and therefore moves between fully closed and allowing a maximum annular space of 2 mm. The hydraulic actuator attached to the valve needle keeps the valve needle moving in and out endlessly, very quickly and with very small movements along the longitudinal axis.

Under certain circumstances, it is desirable to have a continuous processing of materials, liquids, or both under a constant pressure. For example, the pretreatment of biomass is uneconomical in batches. It is time-consuming and wastes materials. The problem is how to keep a constant precise pressure during treatment while moving substances through a pipe or barrel and discharging pressurized materials to atmospheric pressure simultaneously. Further, it is difficult to do this when working with slurries because the nature of the heterogeneous mixture can cause pulsing.

The valve described herein can be used at high velocities. For example, continuous biomass processing as measured at the annular ring 19 is 185-190 m/s at a 0.5 mm stroke. Potential ranges are about 90 m/s to 250 m/s. In other embodiments, velocities of 95 m/s, 100 m/s, 110 m/s, 120 m/s, 130 m/s, 140 m/s, 150 m/s, 160 m/s, 170 m/s, 180 m/s, 190 m/s, 200 m/s, 210 m/s, 220 m/s, 230 m/s, 240 m/s, and higher are possible.

In some embodiments, the liquid or slurry is treated for less than 60, 55, 50, 45, 40, 35, 30, 25, 20, 19, 18, 17, 16, 15, 14, 13, 12, 10, 9, 8, 7, 6, 5, 4, 3, 2, or 1 seconds in the reaction zone. In some embodiments, biomass is treated for about 5 to 15 seconds in the reaction zone; in larger systems, the biomass is treated for 30 seconds or less, or is treated for 60 seconds or less.

In another embodiment, a liquid or slurry can be treated at an elevated pressure. In one embodiment biomass is pretreated at a pressure range of about 1 psi to about 30 psi. In another embodiment biomass is pretreated at a pressure or about 50 psi, 100 psi, 150 psi, 200 psi, 250 psi, 300 psi, 350 psi, 400 psi, 450 psi, 500 psi, 550 psi, 600 psi, 650 psi, 700 psi, 750 psi, 800 psi or more up to 900 psi. In some embodiments, biomass can be treated with elevated pressures by the injection of steam into a biomass containing vessel. In one embodiment, the biomass can be treated to vacuum conditions prior or subsequent to alkaline or acid treatment or any other treatment methods provided herein.

Exemplary Embodiments

Embodiment 1. A valve assembly comprising a housing, a valve body, and a valve needle attached to a tube with an output that flows through the valve assembly, wherein the valve comprises:
  (a) a conical valve needle which is axially displaceable in an annular space of the valve body and on one end has a conical valve needle tip; and
  (b) wherein the downstream inner diameter of the valve body is at least 4% larger than the inner wall of the housing.

Embodiment 2. The valve assembly of embodiment 1, wherein an annular ring is part of the valve body.

Embodiment 3. The valve assembly of embodiment 2, wherein the annular ring is replaceable.

Embodiment 4. The valve assembly of embodiment 1, wherein the housing contains a detachable discharge ring.

Embodiment 5. The valve assembly of embodiment 1, wherein the valve body contains nozzles for the input of a liquid.

Embodiment 6. The valve assembly of embodiment 2, wherein the valve needle seats when closed in the valve body at the discharge ring.

Embodiment 7. The valve assembly of embodiment 1, that forms a part of a reaction zone with the tube.

Embodiment 8. The valve assembly of embodiment 1, wherein the valve needle is attached to an actuator.

Embodiment 9. The valve assembly of embodiment 8, wherein the actuator maintains a pressure on the valve needle.

Embodiment 10. The valve assembly of embodiment 8, wherein the actuator maintains a pressure of over 1,800 lbf on the valve needle.

Embodiment 11. The valve assembly of embodiment 9, wherein the actuator maintains a pressure of between 50,000 to 500,000 lbf on the valve needle.

Embodiment 12. The valve assembly of embodiment 8, wherein the tube is an extruder.

Embodiment 13. The valve assembly of embodiment 13, wherein the extruder is a twin screw extruder.

Embodiment 14. A conical valve needle for engagement with a valve body that comprises a valve needle that extends beyond the valve body into a discharge area when the valve is closed.

Embodiment 15. The valve needle of Embodiment 14, wherein an annular ring is part of the valve body.

Embodiment 16. The valve needle of Embodiment 15, wherein the valve needle seats downstream of the annular ring.

Embodiment 17. The valve needle of Embodiment 15, wherein the annular ring is replaceable.

Embodiment 18. The valve needle of Embodiment 14, wherein a housing is attached downstream to the valve body and contains a detachable discharge ring.

Embodiment 19. The valve needle of Embodiment 14, wherein the valve body contains nozzles for the input of a liquid.

Embodiment 20. The valve needle of Embodiment 14, wherein the valve needle seats when closed in the valve body at the discharge ring.

Embodiment 21. The valve needle of Embodiment 14, that forms a part of a reaction zone with the tube.

Embodiment 22. The valve needle of Embodiment 14, wherein the valve needle is attached to an actuator.

Embodiment 23. The valve needle of Embodiment 22, wherein the actuator maintains a pressure on the valve needle.

Embodiment 24. The valve needle of Embodiment 23, wherein the actuator maintains a pressure of over 1,800 lbf on the valve needle.

Embodiment 25. The valve needle of Embodiment 24, wherein the pressure is between 50,000 to 500,000 lbf on the valve needle.

Embodiment 26. The valve needle of Embodiment 14, wherein valve body is attached to an extruder.

Embodiment 27. The valve needle of Embodiment 1, wherein the extruder is a twin screw extruder.

Embodiment 28. A valve assembly that becomes part of the reaction zone with a tube or pipe.

Embodiment 29. The valve assembly of Embodiment 28, wherein the pipe or tube is an extruder.

Embodiment 30. The valve assembly of Embodiment 29, wherein the extruder is a twin screw extruder.

Embodiment 31. The valve assembly of Embodiment 30, wherein at least part of the contents of the extruder are under pressure.

Embodiment 32. The valve assembly of Embodiment 30, wherein the pressurized zone extends into the valve assembly.

Embodiment 33. A valve assembly that has an increase in internal diameter between the end of the valve body where material is discharged and the diameter of the discharge housing.

Embodiment 34. A valve assembly for use in pressurized passage of a fluid, slurry or other materials comprising:
  (a) a housing;
  (b) a valve body comprising:
    i. a large circular section;
    ii. a middle conical section;
    iii. a smaller circular collar containing one or more nozzles for liquid input; and
  (c) a valve needle.

Embodiment 35. The valve assembly of Embodiment 34, wherein the housing contains a removable discharge ring.

Embodiment 36. The valve assembly of Embodiment 35, wherein the discharge ring is tapered.

Embodiment 37. The valve assembly of Embodiment 34, wherein the valve body contains an annular ring.

Embodiment 38. The valve assembly of Embodiment 37, wherein the annular ring is removable.

Embodiment 39. The valve assembly of Embodiment 34, wherein there is a space between the valve body and the valve needle when the valve needle is seated.

Embodiment 40. The valve assembly of Embodiment 34, wherein the nozzles for liquid input transfer water into the space between the valve body and the valve needle.

Embodiment 41. The valve assembly of Embodiment 34, wherein the nozzles for liquid input transfer a liquid other than water into the space between the valve body and the valve needle.

Embodiment 42. The valve assembly of Embodiment 41, wherein the liquid is selected from the group consisting of: an acid, a base, an alcohol, a ketone, an aldehyde, a solvent, or a combination thereof.

Embodiment 43. A system for treating biomass through an extruder comprising:
  (a) an extruder comprising one or more screws wherein an internal plug of biomass is formed due to action of the screws, thereby forming one end of a pressurized reaction zone;
  (b) a means for supplying steam and chemicals to the reaction zone;
  (c) a valve assembly at the output end of the extruder that forms the downstream end of the reaction zone and adds a liquid to the reaction zone; and
  (d) said valve assembly capable of rapidly discharging pressurized treated biomass into a non-pressurized discharge area.

Embodiment 44. The system of Embodiment 43, wherein the biomass is selected from the group consisting of: silage, agricultural residues, corn stover, bagasse, sorghum, nuts, nut shells, coconut shells, Distillers Dried Solubles, Distillers Dried Grains, Condensed Distillers Solubles Distillers Wet Grains, Distillers Dried Grains with Solubles, woody materials, sawdust, wood chips, timber slash, mill scrap, municipal waste, waste paper, recycled toilet papers, yard clippings, and energy crops such as poplars, willows, switchgrass, alfalfa, and prairie bluestem, non-woody plant matter, cellulosic material, lignocellulosic material, hemicellulosic material, carbohydrates, corn, sugar cane, grasses, switchgrass, high biomass sorghum, bamboo, corncobs, and peels and pits.

Embodiment 45. The system of Embodiment 43, wherein the biomass is treated for less than 60, 55, 50, 45, 40, 35, 30, 25, 20, 19, 18, 17, 16, 15, 14, 13, 12, 10, 9, 8, 7, 6, 5, 4, 3, 2, or 1 second in the reaction zone.

Embodiment 46. The system of Embodiment 43, wherein the temperature in the reaction zone is elevated to 50-500° C., 75-400° C., 100-350° C., 150-300° C., 200-250° C., 150-300° C., 50-1000 PSI, 100-750 PSI, 200-600 PSI, 300-500 PSI or 350-450 PSI.

Embodiment 47. The system of Embodiment 43, wherein the chemical is an acid.

Embodiment 48. The system of Embodiment 47, wherein the acid is sulfuric acid.

Embodiment 49. The system of Embodiment 43, wherein the valve assembly comprises:
  (a) a housing;
  (b) a valve body comprising:
    i. a large circular section;
    ii. a middle conical section;
    iii. a smaller circular collar containing one or more nozzles for liquid input; and
  (c) a valve needle.

Embodiment 50. The valve assembly of Embodiment 49, wherein the housing contains a removable discharge ring.

Embodiment 51. The valve assembly of Embodiment 50, wherein the discharge ring is tapered.

Embodiment 52. The valve assembly of Embodiment 49, wherein the valve body contains an annular ring.

Embodiment 53. The valve assembly of Embodiment 52, wherein the annular ring is removable.

Embodiment 54. The valve assembly of Embodiment 49, wherein there is a space between the valve body and the valve needle when the valve needle is seated.

Embodiment 55. The valve assembly of Embodiment 49, wherein the nozzles for liquid input transfer water into the space between the valve body and the valve needle.

Embodiment 56. The valve assembly of Embodiment 55, wherein the nozzles for liquid input transfer a liquid other than water into the space between the valve body and the valve needle.

Embodiment 57. The valve assembly of Embodiment 56, wherein the liquid is selected from the group consisting of: an acid, a base, an alcohol, a ketone, an aldehyde, a solvent, or a combination thereof.

Embodiment 58. A method for treating a slurry or liquid in a pipe or barrel comprising:
a. a pipe or barrel with a plug forming one end of a reaction zone;
b. moving a liquid or slurry through the pipe or barrel;
c. using a valve assembly attached to the output end of the pipe or barrel to form the downstream end of the reaction zone while maintaining pressure in the reaction zone;
d. adding a liquid into the upstream end of the valve assembly as the liquid or slurry enters the valve assembly: and
e. using the valve assembly to discharge treated liquid or slurry into a non-pressurized area.

Embodiment 59. A valve assembly attached to a pipe or barrel that inputs a liquid into the valve body after output of a liquid or slurry from the pipe or barrel but before said liquid or slurry reaches the valve needle.

Embodiment 60. A valve assembly wherein the valve body has a removable annular ring adjacent to a removable discharge ring in the discharge housing.

Embodiment 61. The valve assembly of Embodiment 60, wherein the discharge ring is tapered.

[1] A valve assembly comprising:
a valve body having an input end, a discharge end, and a chamber formed therein in connection with the input end and the discharge end, the input end attachable to a tube with a fluid or slurry input that flows through the valve assembly;
a conical valve needle that has a cone with a wide end opposing to its conical tip and is axially displaceable in the chamber within the valve body; and
a housing attached to the discharge end of the valve body and enclosing the valve needle when the valve needle is disengaged with the valve body;
wherein the valve needle has a diameter at the wide end that is at least 4% larger than an inner diameter of the valve body at its discharge end.

[2] The valve assembly of paragraph [1], wherein the valve body has an annular ring that sits in a recessed cavity on an internal surface of the valve body at the discharge end.

[3] The valve assembly of paragraph [2], wherein the annular ring is replaceable.

[4] The valve assembly of paragraph [2] or [3], wherein an internal surface of the annular ring aligns with the internal surface of the valve body.

[5] The valve assembly of any one of paragraphs [2]-[4], wherein the valve needle sits at the annular ring when closed in the valve body.

[6] The valve assembly of any one of paragraphs [1]-[5], wherein the housing comprises therein a detachable discharge ring that sits adjacent to the discharge end of the valve body.

[7] The valve assembly of paragraph [6], wherein the discharge ring has a tapered shape.

[8] The valve assembly of any one of paragraphs [1]-[7] [8][9], wherein the valve body comprises nozzles for input of a liquid.

[9] The valve assembly of any one of paragraphs [1]-[8], wherein the chamber of the valve body forms a part of a reaction zone with the tube for a biomass pretreatment process.

[10] The valve assembly of paragraph [9], wherein the tube is an extruder.

[11] The valve assembly of paragraph [10], wherein the extruder is a twin screw extruder.

[12] The valve assembly of any one of paragraphs [1]-[11], wherein the valve needle is operably linked to an actuator via a shaft.

[13] The valve assembly of paragraph [12], wherein the actuator maintains a pressure on the valve needle.

[14] The valve assembly of paragraph [12] or [13], wherein the actuator maintains a pressure of over 1,800 lbf on the valve needle.

[15] The valve assembly of any one of paragraphs [12]-[14], wherein the actuator maintains a pressure of between 50,000 to 500,000 lbf on the valve needle.

[16] The valve assembly of any one of paragraphs [1]-[15], wherein the valve body has a circular section at the discharge end, a circular collar at the input end that is smaller in inner diameter than the circular section at the discharge end, and an intercalary conical section therebetween.

[17] The valve assembly of any one of paragraphs [1]-[16], wherein there is an annular space formed in the chamber between the valve needle and the valve body when the valve needle is closed on the valve body.

[18] The valve assembly of any one of paragraphs [1]-[17], wherein the housing comprises a discharge pipe.

[19] The valve assembly of any one of paragraphs [1]-[18], wherein an inner diameter of the housing at an end of the housing abutting the valve body is at least 7% larger than an inner diameter of the valve body at its discharge end.

[20] The valve assembly of any one of paragraphs [1]-[19], wherein an inner diameter of the housing at an end of the housing abutting the valve body is about 7% larger than an inner diameter of the valve body at its discharge end.

[21] The valve assembly of any one of paragraphs [1]-[20], wherein the cone of the conical valve needle is tapered in a range of from about 45 degrees to about 75 degrees.

[22] The valve assembly of any one of paragraphs [1]-[21], wherein the cone of the conical valve needle is tapered about 45 degrees.

[23] A conical valve needle for engagement with a valve body that comprises a valve needle that extends beyond the valve body into a discharge area when the valve is closed.

[24] The valve needle of paragraph [23], wherein an annular ring is part of the valve body.

[25] The valve needle of paragraph [24], wherein the valve needle seats downstream of the annular ring.

[26] The valve needle of paragraph [24] or [25], wherein the annular ring is replaceable.

[27] The valve needle of any one of paragraphs [23]-[26] [27][28][30][31], wherein a housing is attached downstream to the valve body and contains a detachable discharge ring.

[28] The valve needle of any one of paragraphs [23]-[27], wherein the valve body contains nozzles for the input of a liquid.

[29] The valve needle of any one of paragraphs [23]-[28], wherein the valve needle seats when closed in the valve body at the discharge ring.

[30] The valve needle of any one of paragraphs [23]-[29], that forms a part of a reaction zone with the tube.

[31] The valve needle of any one of paragraphs [23]-[30], wherein the valve needle is attached to an actuator.

[32] The valve needle of paragraph [31], wherein the actuator maintains a pressure on the valve needle.

[33] The valve needle of paragraph [32], wherein the actuator maintains a pressure of over 1,800 lbf on the valve needle.

[34] The valve needle of paragraph [33], wherein the pressure is between 50,000 to 500,000 lbf on the valve needle.

[35] The valve needle of any one of paragraphs [23]-[34], wherein valve body is attached to an extruder.

[36] The valve needle of paragraph [35], wherein the extruder is a twin screw extruder.

[37] A valve assembly that becomes part of the reaction zone with a tube or pipe.

[38] The valve assembly of paragraph [37], wherein the pipe or tube is an extruder.

[39] The valve assembly of paragraph [38], wherein the extruder is a twin screw extruder.

[40] The valve assembly of paragraph [39], wherein at least part of the contents of the extruder are under pressure.

[41] The valve assembly of paragraph [39], wherein the pressurized zone extends into the valve assembly.

[42] A valve assembly that has an increase in internal diameter between the end of the valve body where material is discharged and the diameter of the discharge housing.

[43] A valve assembly comprising:
a valve body comprising a large circular section, an intercalary conical section, and a small circular collar containing one or more nozzles for liquid input, the valve body having a chamber formed therein that connects an input end and a discharge end of the valve body, wherein the small circular collar is smaller in inner diameter than the large circular section;
a valve needle axially displaceable within the chamber of the valve body; and
a housing attached to the discharge end of the valve body and enclosing the valve needle when the valve needle is disengaged with the valve body.

[44] The valve assembly of paragraph [43], wherein the housing contains a removable discharge ring.

[45] The valve assembly of paragraph [44], wherein the discharge ring is tapered.

[46] The valve assembly of any one of paragraphs [43]-[45], wherein the valve body contains an annular ring.

[47] The valve assembly of paragraph [46], wherein the annular ring is removable.

[48] The valve assembly of any one of paragraphs [43]-[47], wherein there is an annular space formed in the chamber between the valve body and the valve needle when the valve needle is closed on the valve body.

[49] The valve assembly of any one of paragraphs [43]-[48] [49], wherein the nozzles for liquid input transfer water into the chamber.

[50] The valve assembly of any one of paragraphs [43]-[49], wherein the nozzles for liquid input transfer a liquid other than water into the chamber.

[51] The valve assembly of paragraph [50], wherein the liquid is selected from the group consisting of: an acid, a base, an alcohol, a ketone, an aldehyde, a solvent, or a combination thereof.

[52] The valve assembly of any one of paragraphs [43]-[51], wherein an inner diameter of the housing at an end of the housing abutting the valve body is at least 7% larger than an inner diameter of the valve body at its discharge end.

[53] The valve assembly of any one of paragraphs [43]-[52], wherein an inner diameter of the housing at an end of the housing abutting the valve body is about 7% larger than an inner diameter of the valve body at its discharge end.

[54] The valve assembly of any one of paragraphs [43]-[53], wherein the valve needle has a cone with a wide end opposing to its conical tip.

[55] The valve assembly of paragraph [54], wherein the cone is tapered in a range of from 45 degrees to 75 degrees.

[56] The valve assembly of paragraph [54], wherein the cone is tapered about 45 degrees.

[57] The valve assembly of any one of paragraphs [54]-[56], wherein the valve needle has a diameter at the wide end that is at least 4% larger than an inner diameter of the valve body at its discharge end.

[58] The valve assembly of any one of paragraphs [54]-[56], wherein the valve needle has a diameter at the wide end that is about 4% larger than an inner diameter of the valve body at its discharge end.

[59] A system for treating biomass through an extruder comprising:
(a) an extruder comprising one or more screws wherein an internal plug of biomass is formed due to action of the screws, thereby forming one end of a pressurized reaction zone;
(b) a means for supplying steam and chemicals to the reaction zone; and
(c) a valve assembly at an output end of the extruder that forms a downstream end of the reaction zone and adds a liquid to the reaction zone;
wherein the valve assembly is capable of rapidly discharging pressurized treated biomass into a non-pressurized discharge area.

[60] The system of paragraph [59], wherein the biomass is selected from the group consisting of: silage, agricultural residues, corn stover, bagasse, sorghum, nuts, nut shells, coconut shells, Distillers Dried Solubles, Distillers Dried Grains, Condensed Distillers Solubles Distillers Wet Grains, Distillers Dried Grains with Solubles, woody materials, sawdust, wood chips, timber slash, mill scrap, municipal waste, waste paper, recycled toilet papers, yard clippings, and energy crops such as poplars, willows, switchgrass, alfalfa, and prairie bluestem, non-woody plant matter, cellulosic material, lignocellulosic material, hemicellulosic material, carbohydrates, corn, sugar cane, grasses, switchgrass, high biomass sorghum, bamboo, corncobs, and peels and pits.

[61] The system of paragraph [59] or [60], wherein the biomass is treated for less than 60, 55, 50, 45, 40, 35, 30, 25, 20, 19, 18, 17, 16, 15, 14, 13, 12, 10, 9, 8, 7, 6, 5, 4, 3, 2, or 1 second in the reaction zone.

[62] The system of any one of paragraphs [59]-[61], wherein the temperature in the reaction zone is elevated to 50-500° C., 75-400° C., 100-350° C., 150-300° C., 200-250° C., 150-300° C., 50-1000 PSI, 100-750 PSI, 200-600 PSI, 300-500 PSI or 350-450 PSI.

[63] The system of any one of paragraphs [59]-[62], wherein the chemical is an acid.

[64] The system of paragraph [63], wherein the acid is sulfuric acid.

[65] The system of any one of paragraphs [59]-[64], wherein the valve assembly comprises:
a valve body comprising a large circular section, an intercalary conical section, and a small circular collar containing one or more nozzles for liquid input, the valve body having a chamber formed therein that connects an input end and a discharge end of the valve body, wherein the small circular collar is smaller in inner diameter than the large circular section;
a valve needle axially displaceable within the chamber of the valve body; and a housing attached to the discharge end of the valve body and enclosing the valve needle when the valve needle is disengaged with the valve body.

[66] The system of paragraph [65], wherein the housing contains a removable discharge ring.

[67] The system of paragraph [66], wherein the discharge ring is tapered.

[68] The system of any one of paragraphs [65]-[67], wherein the valve body contains an annular ring.

[69] The system of paragraph [68], wherein the annular ring is removable.

[70] The system of any one of paragraphs [65]-[69], wherein there is an annular space formed in the chamber between the valve body and the valve needle when the valve needle is closed on the valve body.

[71] The system of any one of paragraphs [65]-[70], wherein the nozzles for liquid input transfer water into the chamber.

[72] The system of any one of paragraphs [65]-[71], wherein the nozzles for liquid input transfer a liquid other than water into the chamber.

[73] The system of paragraph [72], wherein the liquid is selected from the group consisting of: an acid, a base, an alcohol, a ketone, an aldehyde, a solvent, or a combination thereof.

[74] The system of any one of paragraphs [65]-[73], wherein an inner diameter of the housing at an end of the housing abutting the valve body is at least 7% larger than an inner diameter of the valve body at its discharge end.

[75] The system of any one of paragraphs [65]-[74], wherein an inner diameter of the housing at an end of the housing abutting the valve body is about 7% larger than an inner diameter of the valve body at its discharge end.

[76] The system of any one of paragraphs [65]-[75], wherein the valve needle has a cone with a wide end opposing to its conical tip.

[77] The system of paragraph [76], wherein the cone is tapered in a range of from 45 degrees to 75 degrees.

[78] The system of paragraph [76], wherein the cone is tapered about 45 degrees.

[79] The system of any one of paragraphs [76]-[78], wherein the valve needle has a diameter at the wide end that is at least 4% larger than an inner diameter of the valve body at its discharge end.

[80] The system of any one of paragraphs [76]-[78], wherein the valve needle has a diameter at the wide end that is about 4% larger than an inner diameter of the valve body at its discharge end.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A valve assembly comprising:
 a valve body having an input end, a discharge end, and a chamber formed therein in connection with the input end and the discharge end, wherein the input end is attachable to a tube with a fluid or slurry input that flows through the valve assembly, wherein the valve body has a first circular collar at the input end, a second circular section at the discharge end, and an intercalary conical section therebetween, and wherein the first circular collar is smaller in inner diameter than the second circular section;
 a conical valve needle that has a cone with a wide end opposing to its conical tip and is axially displaceable in the chamber within the valve body, wherein the conical valve needle abuts the valve body at the discharge end of the valve body when the conical valve needle is closed on the valve body; and
 a housing attached to the discharge end of the valve body and enclosing the conical valve needle when the conical valve needle is disengaged with the valve body;
 wherein the conical valve needle has a diameter at the wide end that is at least 4% larger than an inner diameter of the valve body at its discharge end.

2. The valve assembly of claim 1, wherein the valve body has an annular ring that sits in a recessed cavity on an internal surface of the valve body at the discharge end.

3. The valve assembly of claim 2, wherein the annular ring is replaceable.

4. The valve assembly of claim 2, wherein an internal surface of the annular ring aligns with the internal surface of the valve body.

5. The valve assembly of claim 2, wherein the conical valve needle sits at the annular ring when closed in the valve body.

6. The valve assembly of claim 1, wherein the housing comprises therein a detachable discharge ring that sits adjacent to the discharge end of the valve body.

7. The valve assembly of claim 6, wherein the discharge ring has a tapered shape.

8. The valve assembly of claim 1, wherein the valve body comprises nozzles for input of a liquid.

9. The valve assembly of claim 1, wherein the chamber of the valve body forms a part of a reaction zone with the tube for a biomass pretreatment process.

10. The valve assembly of claim 9, wherein the tube is an extruder.

11. The valve assembly of claim 10, wherein the extruder is a twin screw extruder.

12. The valve assembly of claim 1, wherein the valve assembly further comprises an actuator and a shaft, and wherein the conical valve needle is operably linked to the actuator via the shaft.

13. The valve assembly of claim 12, wherein the actuator maintains a pressure on the conical valve needle.

14. The valve assembly of claim 12, wherein the actuator is configured to maintain a pressure of over 1,800 lbf on the conical valve needle.

15. The valve assembly of claim 1, wherein there is an annular space formed in the chamber between the conical valve needle and the valve body when the conical valve needle is closed on the valve body.

16. The valve assembly of claim 1, wherein an inner diameter of the housing at an end of the housing abutting the valve body is at least 7% larger than an inner diameter of the valve body at its discharge end.

17. The valve assembly of claim 1, wherein the cone of the conical valve needle is tapered in a range of from about 45 degrees to about 75 degrees.

18. The valve assembly of claim 1, wherein the cone of the conical valve needle is tapered about 45 degrees.

19. A valve assembly comprising:
 a valve body comprising (1) a large circular section, a small circular collar, and an intercalary conical section therebetween, and (2) one or more nozzles for liquid input, the valve body having a chamber formed therein that connects an input end and a discharge end of the valve body, wherein the small circular collar is at the input end and the large circular section is at the discharge end, and wherein the small circular collar is smaller in inner diameter than the large circular section;

a conical valve needle axially displaceable within the chamber of the valve body, wherein the conical valve needle abuts the valve body at the discharge end of the valve body when the conical valve needle is closed on the valve body; and a housing attached to the discharge end of the valve body and enclosing the valve needle when the valve needle is disengaged with the valve body.

* * * * *